United States Patent [19]
Baier et al.

[11] Patent Number: 4,466,277
[45] Date of Patent: Aug. 21, 1984

[54] THERMAL CHAMBERED FLOW CELL

[75] Inventors: Robert E. Baier, Eggertsville; Raymond W. King, Buffalo; Anne E. Meyer, N. Tonawanda, all of N.Y.

[73] Assignee: Calspan Corporation, Buffalo, N.Y.

[21] Appl. No.: 452,244

[22] Filed: Dec. 22, 1982

[51] Int. Cl.³ ............................................. G01N 17/00
[52] U.S. Cl. ................................................... 73/61.2
[58] Field of Search ........................ 73/61.2; 374/6, 7; 165/11 R, 140, 141; 250/343; 422/53

[56] References Cited

U.S. PATENT DOCUMENTS

| | | | |
|---|---|---|---|
| 3,108,468 | 10/1963 | Mickel | 73/61.2 |
| 3,918,300 | 11/1975 | Weisstuch et al. | 374/7 |
| 4,044,605 | 8/1977 | Bratthall | 73/61.2 |
| 4,175,233 | 11/1979 | De Palma et al. | 250/343 |
| 4,346,587 | 8/1982 | Brindak | 73/61.2 |

Primary Examiner—Gerald Goldberg
Assistant Examiner—Hezron E. Williams
Attorney, Agent, or Firm—Biebel, French & Nauman

[57] ABSTRACT

A flow cell for monitoring accumulations of microscopic material in heat exchange systems and the like, by measuring accretion on the surfaces of a pair of plates exposed to a primary flow, includes a split housing which supports the pair of plates in closely spaced relation with an inlet and an outlet positioned to apply a primary flow between the plates, and further includes a cavity formed in each housing half with the back or opposite sides of the plates exposed to the interior of the cavity and fluid inlets and outlets leading into such cavities providing for the flow of a secondary fluid through the cavities and across the back sides of the plates for the purpose of more accurately simulating the thermal gradient conditions on the plates in a heat exchanger, and for monitoring the rate of accumulation on the plate surfaces.

4 Claims, 3 Drawing Figures

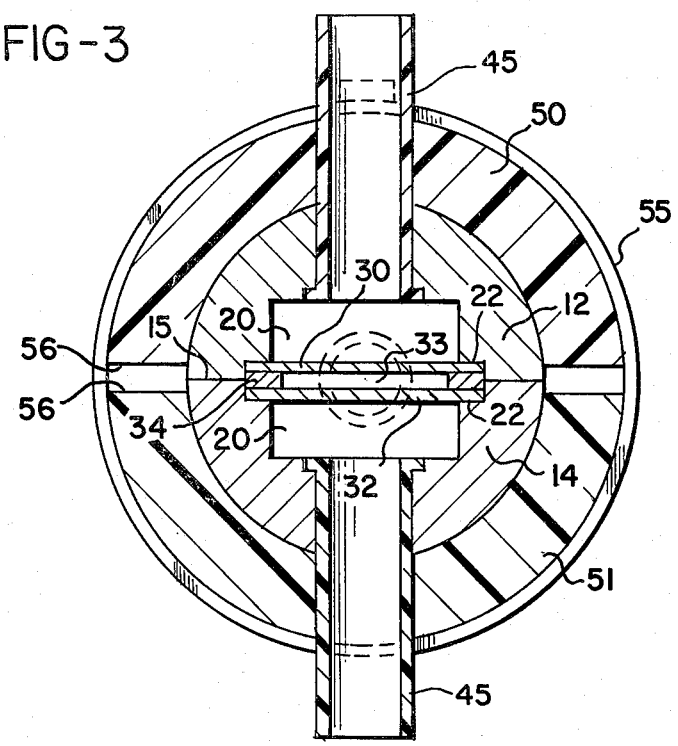

THERMAL CHAMBERED FLOW CELL

This invention relates to thermal chambered flow cells of the kind as described and claimed in the patent of DePalma et al, U.S. Pat. No. 4,175,233 issued Nov. 20, 1979 and assigned to the same assignee as this invention. The disclosure of the DePalma et al patent is specifically incorporated into this specification by reference.

In DePalma, a flow cell and method are disclosed which permit a convenient analysis of films which accumulate on the interior surfaces of a pair of spaced apart plates when a liquid is flowed between the plates. In practice, such cells are used, for example, in heat exchanger systems in order to sample and analyze deposits on the inside surfaces thereof as indicative of or as representing deposits which will be or are being formed on interior exposed plates and surfaces of the heat exchanger itself. Such analysis of the surfaces exposed to flow within the cell has provided an early opportunity to take preventive or corrective measures, as necessary.

In many instances, however, it has not been possible accurately to simulate actual heat exchanger conditions, and the build-up or rate or build-up on the cell surfaces has not always conformed to actual conditions in view of the fact that the test plates themselves have not been subject to those conditions under which the walls of a heat exchanger operate. Such heat exchanger walls commonly have a concurrent or counter-current flow of a liquid or gas phase on the back or opposite surfaces thereof, at a higher or lower temperature, providing a temperature gradient in the wall and an inflow or outflow of heat energy through the wall. Such temperature gradient or energy flow-through conditions may have an effect upon the rate and or character of accretion on heat exchanger walls which heretofore has not been accurately duplicated in flow cells made according to the DePalma disclosure.

SUMMARY OF THE INVENTION

This invention is directed to an improved flow cell of the kind disclosed in the above identified DePalma et al patent, further including one or more cavities formed in communication with the outside surfaces of the operative test plates, together with passages for admitting and flowing a secondary fluid therepast. More particularly, the flow cell of this invention is provided with spaces behind each of the flow cell test plates formed in the two halves making up the body of the cylindrical holder, together with separate entry and/or exit ports for each of the cavities, to provide for a secondary fluid flow across the back or opposite surfaces of the test plates. In this manner a flow cell may more nearly duplicate the actual or anticipated conditions of operation in a heat exchanger or the like.

It is accordingly an important object of this invention to provide an improved flow cell incorporating a pair of closely spaced test plates, such as germanium test plates or the like, together with means for directing a primary fluid flow between the adjacent surfaces of the test plates and means in the cell for directing a secondary fluid flow across one or both of the opposite surfaces of the test plates.

Another object of the invention is the provision of a demountable flow cell including a pair of mating housing members which have correspondingly inwardly facing recesses which respectively receive first and second test plates therebetween, including means for separating the plates when assembled to define a flow path therebetween in combination with means in the mating housing members for receiving a second fluid flow therethrough in contact with the opposite surfaces of such plates to simulate actual conditions in a heat exchanger or the like.

These and other objects and advantages of the invention will be apparent from the following description, the accompanying drawings, and the appended claims.

BRIEF DESCRIPTION OF THE DRAWINGS

FIG. 3 is a transverse section therethrough looking generally along the line 3—3 of FIG. 2.

DESCRIPTION OF THE PREFERRED EMBODIMENT

Figure 1:
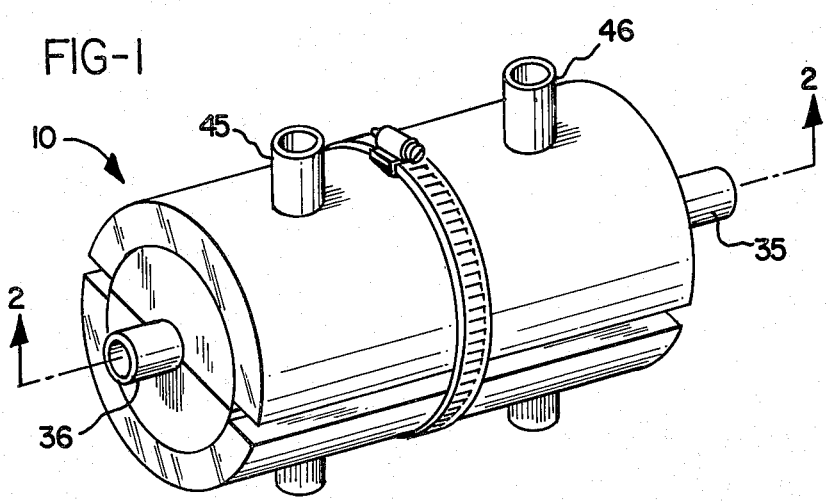
FIG. 1 is a perspective view of the flow cell of this invention.

Referring to the figures of the drawing which illustrate a preferred embodiment of the invention, a flow cell constructed according to the invention is illustrated generally at 10 in FIG. 1. The flow cell, as shown, is adapted to be connected in line within a heat exchange system or the like for monitoring the fouling conditions within the primary fluid flowing within the heat exchanger, for an example. The cell 10 shown in FIG. 1 is in its closed or ready to use condition. Thus, the cell is provided with two semi-cylindrical matching housing sections or body members 12 and 14. The body members mate together at a common mating plane 15 to form a single cylindrical body.

Each of the housing members 12 and 14 is provided with an internal matching relieved portion defining an internal generally rectangularly shaped cavity 20, which cavity is stepped or formed with a ledge 22 around its margins to receive a pair of spaced-apart test plates 30 and 32 therebetween. The plates 30 and 32 are separated from each other by means of longitudinally extending shims 34 when the two halves or sections of the body are brought together. As shown in FIG. 3, the depth of the ledge 22 exceeds the thickness of either plate 30 or 32 so that an internal cavity or passage 33 is formed between the adjacent plate surfaces and the shims.

The body halves are preferably formed from an inert silicone polymer such as "Sylgard" of Dow Chemical Corporation, Midland, Mich., which has good thermal insulation properties and the necessary strength to support the test plates 30 and 32. The shims may be formed of the same material as the body, or alternatively, may be formed of glass or other suitable material relatively inert to the fluid which will flow between the plates.

The plates themselves are advantageously formed of germanium which are transparent to infrared radiation, as set out in more detail in DePalma et al, and may have the physical dimensions as set forth in that patent.

Figure 2:
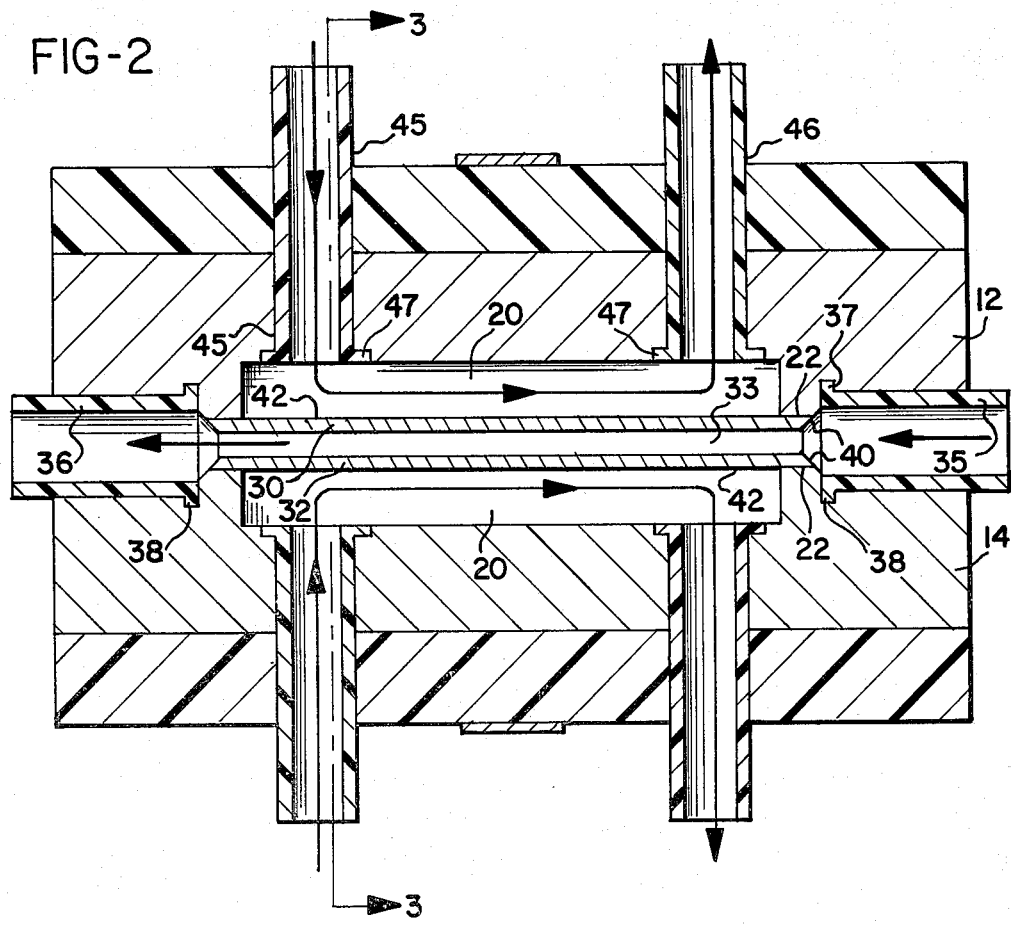
FIG. 2 is an enlarged longitudinal section through the fuel cell looking generally along the line 2—2 of FIG. 1.

Means for admitting a primary fluid flow into the passage 33 defined between the spaced-apart test plates 30 and 32 include inlet tubes 35 and 36 which are clamped between the body halves 12 and 14 and which open into the space 33. For this purpose, the tubes 35 and 36 are formed with flanged inner ends 37 received within cooperating semi-circular recesses 38 formed in the body members to trap the tubes therein when the members are assembled at the parting plane 15. Each body member 12 and 14 is formed with a relieved portion shown generally at 40 in FIG. 2 so as to define therebetween an opening which communicates into the interior of the inlet tubes 35 and 36 on the one hand and into the passage 33 between the test plates 30 and 32, providing for the flow of a primary fluid between the plates to be monitored for microdeposition therefrom onto the inside surfaces of the test plates.

As previously noted, in the DePalma construction, it was not possible fully to simulate the conditions which occur within a heat exchanger in actual use by reason of the fact that a thermal gradient is formed on the plates of the heat exchanger, and the thermal gradient itself has an effect upon the character or rate of deposition on the heat exchanger plates. The flow cell of the present invention is adapted for more closely simulating the actual conditions of a heat exchanger by means of provision for the application of a secondary fluid to the obverse or back surfaces 42 of the plates 30 and 32, such that the plates themselves may function as a heat transfer wall permitting inflow or outflow of thermal energy therethrough from first and second fluid mediums. Either the first or second fluid medium or both may thus be a liquid or a gas in accordance with desired conditions. For this purpose, when the plates are assembled on their respective body members, the cavity 20 which is formed above each plate, to form a thermal chamber or passage which is in association with a major portion of the upper surfaces 42 of each plate 30 or 32. The thermal chambers or passages provided above and below the plates are physically isolated from each other so that the same or different materials may be directed therethrough in the same or in different directions to provide a concurrent or countercurrent flow, at different temperatures or rates, as desired.

Means for admitting such secondary flow into and out of the cavities 20 include additional inlet and outlet tubes 45 and 46 corresponding in structure to, for convenience, tubes 35 and 36. The tubes 45 and 46 are tightly fitted through suitable openings formed radially through the body halves and into the interior of the cavities 20, adjacent the axial terminals ends thereof with the flanges 47 thereon received immediately inwardly of the chambers and captured within premolded recesses.

The entire body halves 14 and 15 are preferably substantially enclosed within a pair of partially encircling insulating structural clamping halves 50 and 51, as best shown in the transverse section of FIG. 3. Aligned radially extending passageways are formed in the clamping halves 50 and 51 corresponding to those formed in the body sections, through which the tubes 45 and 46 may be extended from the exterior of the cell 10. The clamping halves themselves are preferably encircled by a stainless steel hose clamp 55, and since the longitudinal marginal edges 56 of the clamping halves do not normally meet, but form a clearance therebetween, as shown in FIG. 3, tightening the hose clamp 55 brings a compression pressure to bear against the body members 12 and 13 and firmly clamps the halves together, capturing the test plates 30 and 32 therebetween as spaced by the shims 34, and further trapping and encapturing the inlet and outlet tubes 35 and 36. Thus, the test cell may be readily disassembled by removing the hose clamp 55, removing the clamping halves 50 and 51, and then parting the body halves 12 and 14 for access to the test plates.

In use, any suitable fluid mediums may be applied to the cavities 20 or 33 at temperatures to simulate or duplicate actual conditions within the heat exchanger itself. If desired, the deposits formed on the back surfaces of the plates exposed to the chambers may be examined independently of or in addition to the deposits formed on the opposed inside surfaces exposed to the primary fluid flow, and computer analysis may be used to subtract known adsorption characteristics of material deposited on such back surfaces or otherwise to make comparisons between the surfaces.

While the form of apparatus herein described constitutes a preferred embodiment of this invention, it is to be understood that the invention is not limited to this precise form of apparatus, and that changes may be made therein without departing from the scope of the invention which is defined in the appended claims.

What is claimed is:

1. A flow cell for monitoring accumulations of microscopic material on surfaces of plates exposed to a primary flow of fluid, comprising:
   means defining a housing,
   means in said housing supporting a pair of plates in closely spaced relation,
   means in said housing for applying a flow of primary fluid to be monitored through the space between said plates and in contact with the adjacent surfaces of said plates,
   means in said housing defining a pair of chambers, one each positioned at the opposite side of each of said plates with said plate opposite sides at least partially forming a closure wall to its associated said chamber, and
   means in said housing for admitting a secondary fluid flow into said chambers for contact with the opposite surfaces of said plates.

2. A demountable flow cell having an inlet and an outlet with a flow path therebetween, comprising:
   a pair of mating housing members,
   first and second plates received respectively in said housing members, said plates having inside and outside surfaces,
   shim means for separating said first and second plates when said flow cell is assembled to define with the inside surface of said plates a portion of said flow path, providing for the flow of a primary fluid therethrough which is to be monitored by said cell,
   means in each of said housing members defining a recess at the outside surface of said plates opposite said primary flow path, and
   inlet and outlet means opening into each of said recesses providing for flow of a secondary fluid therethrough along said outside surfaces of said plates.

3. A flow cell for monitoring accumulations of microscopic material on surfaces of plates exposed to a primary flow of fluid, comprising:
   means defining a housing,
   means in said housing supporting a pair of plates in closely spaced relation,
   means in said housing for applying a primary flow of liquid to be monitored through the space between said plates and in contact with the adjacent surfaces of said plates,
   means in said housing defining at least one chamber positioned at the opposite side of one of said plates, and means in said housing for admitting a secondary fluid flow into said chamber for contact with said one plate.

4. A demountable flow cell having an inlet and an outlet with a flow path therebetween, comprising:
  a pair of mating housing members,
  first and second plates received respectively in said housing members in spaced rotation and defining said flow path therebetween,
  shims for separating said first and second plates when said flow cell is assembled to define with said plates a portion of said flow path,
  means in each of said housing members defining a cavity on the side of said plates opposite said flow path, each of said cavities being at least partially closed by one of said plates so that fluid in the cavity is in contact with a plate at a side thereof remote from said flow path, and
  inlet and outlet means opening into each of said cavities providing for a flow of a secondary fluid therethrough in contact with said plates.

* * * * *